(12) United States Patent
Hawkinson et al.

(10) Patent No.: US 8,935,882 B2
(45) Date of Patent: *Jan. 20, 2015

(54) METHODS FOR CONTROLLING WEEDS AND WATER USING A BAG FILLED WITH LANDSCAPING MATERIAL

(71) Applicant: R & J East, Inc., Jacksonville, FL (US)

(72) Inventors: Robert Neal Alfred Hawkinson, Orange Park, FL (US); James Earl Hawkinson, Orange Park, FL (US)

(73) Assignee: R & J East, Inc., Jacksonville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/157,650

(22) Filed: Jan. 17, 2014

(65) Prior Publication Data
US 2014/0219731 A1    Aug. 7, 2014

Related U.S. Application Data

(63) Continuation-in-part of application No. 13/959,204, filed on Aug. 5, 2013, which is a continuation-in-part of application No. 12/795,841, filed on Jun. 8, 2010, now Pat. No. 8,522,476.

(51) Int. Cl.
| | |
|---|---|
| *A01G 7/00* | (2006.01) |
| *A01G 9/02* | (2006.01) |
| *A01C 14/00* | (2006.01) |
| *A01N 25/00* | (2006.01) |
| *E02D 31/00* | (2006.01) |
| *A01G 13/00* | (2006.01) |
| *E02D 17/20* | (2006.01) |

(52) U.S. Cl.
CPC ............... *A01C 14/00* (2013.01); *A01N 25/00* (2013.01); *E02D 31/00* (2013.01); *A01G 13/0268* (2013.01); *E02D 17/202* (2013.01)
USPC ................................. 47/65.8; 47/9

(58) Field of Classification Search
CPC ....... A01G 7/00; A01G 9/02; A01G 13/0268; E02D 31/00; E02D 17/202
USPC ................................. 47/9, 65.8, 56
See application file for complete search history.

(56) References Cited

U.S. PATENT DOCUMENTS

| | | | |
|---|---|---|---|
| 2,309,702 | A | 1/1943 | Kirschenbaum |
| 3,005,287 | A | 8/1959 | Dudley |
| 3,839,139 | A | 10/1974 | Ito et al. |
| 3,870,583 | A | 3/1975 | Gidge |
| 3,888,418 | A | 6/1975 | Seith et al. |
| 3,962,823 | A | 6/1976 | Zipperer, III |
| 4,090,325 | A | 5/1978 | Mushin et al. |
| 4,209,945 | A | 7/1980 | Dent et al. |
| 4,545,145 | A | 10/1985 | Torrance |

(Continued)

*Primary Examiner* — Monica Williams
(74) *Attorney, Agent, or Firm* — Smith Gambrell & Russell LLP

(57) ABSTRACT

A bag constructed of a weed suppression material for packaging a ground cover material. When the bag is in a closed configuration, the bag serves as a container for shipping, handling, and storage of the ground cover material. When the bag is opened and unfolded, and the ground cover material within the bag is spread over the opened and unfolded bag, the bag serves as a layer of weed suppression material on top of underlying soil and beneath the ground cover. In addition, the bag may be used for planting individual plants in a planting bed, for establishing a buffer zone around the foundation of a building, or for controlling erosion around a downspout of a building.

33 Claims, 7 Drawing Sheets

(56) References Cited

U.S. PATENT DOCUMENTS

| | | |
|---|---|---|
| 4,782,626 A | 11/1988 | Shanley et al. |
| 5,193,306 A | 3/1993 | Whisenant |
| 5,241,783 A | 9/1993 | Krueger |
| 5,389,116 A | 2/1995 | Byrd |
| 5,421,123 A | 6/1995 | Sakate et al. |
| 5,524,387 A | 6/1996 | Whisenant |
| 6,016,628 A | 1/2000 | Schlosser |
| 6,185,864 B1 | 2/2001 | Lee |
| 6,233,867 B1 | 5/2001 | Gibson |
| 6,312,823 B1 | 11/2001 | El-Afandi et al. |
| 6,412,218 B2 | 7/2002 | Lee |
| 6,446,386 B1 | 9/2002 | Holloway |
| 6,523,989 B2 | 2/2003 | Carty |
| 6,681,521 B1 | 1/2004 | Holloway |
| 7,303,084 B2 | 12/2007 | McPhillips |
| 7,303,670 B2 | 12/2007 | McPhillips |
| 7,422,682 B2 | 9/2008 | McPhillips |
| 2003/0044242 A1 | 3/2003 | Chen |
| 2004/0103580 A1 | 6/2004 | Huang et al. |
| 2005/0025397 A1 | 2/2005 | Zhao |
| 2005/0064136 A1 | 3/2005 | Turner et al. |
| 2005/0161407 A1 | 7/2005 | McPhillips |
| 2006/0185235 A1 | 8/2006 | Bono |
| 2007/0251191 A1 | 11/2007 | Maltais et al. |
| 2007/0283621 A1 | 12/2007 | Holloway |
| 2009/0158646 A1 | 6/2009 | Moore, Jr. et al. |

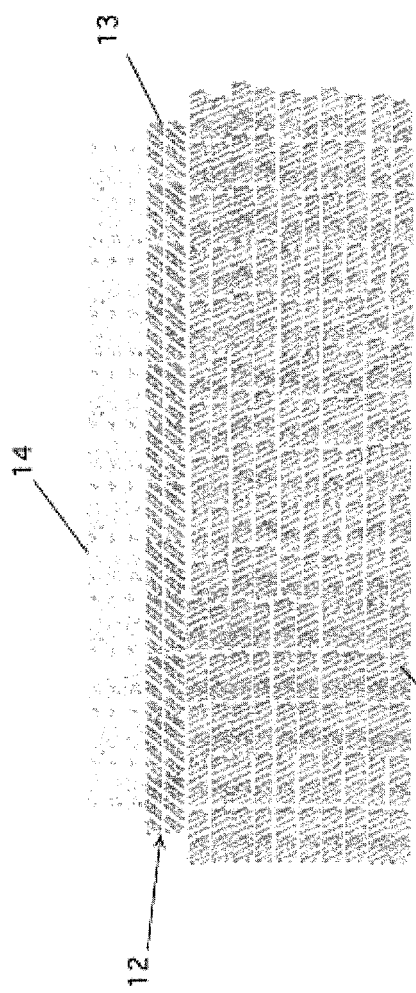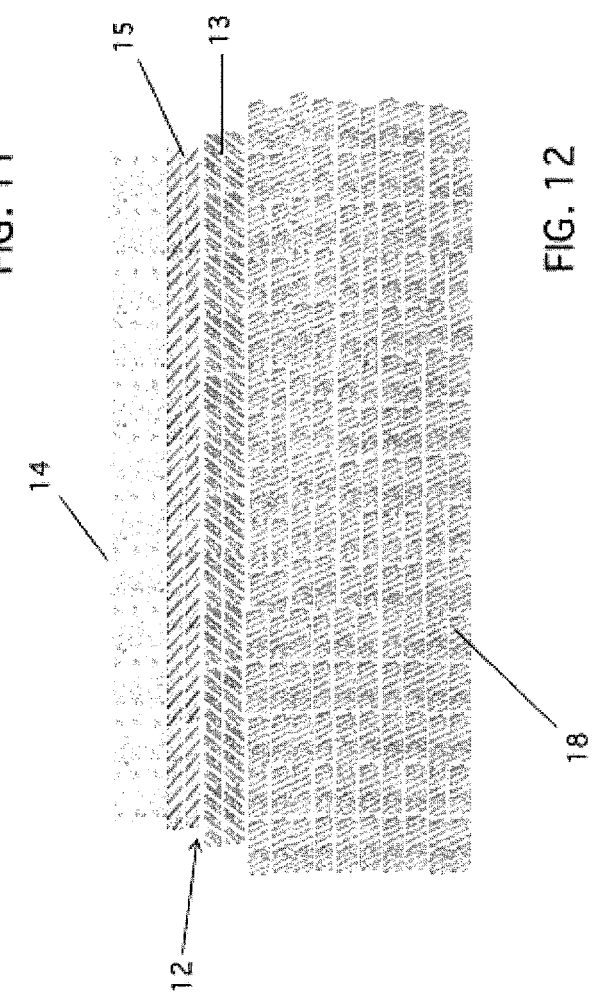

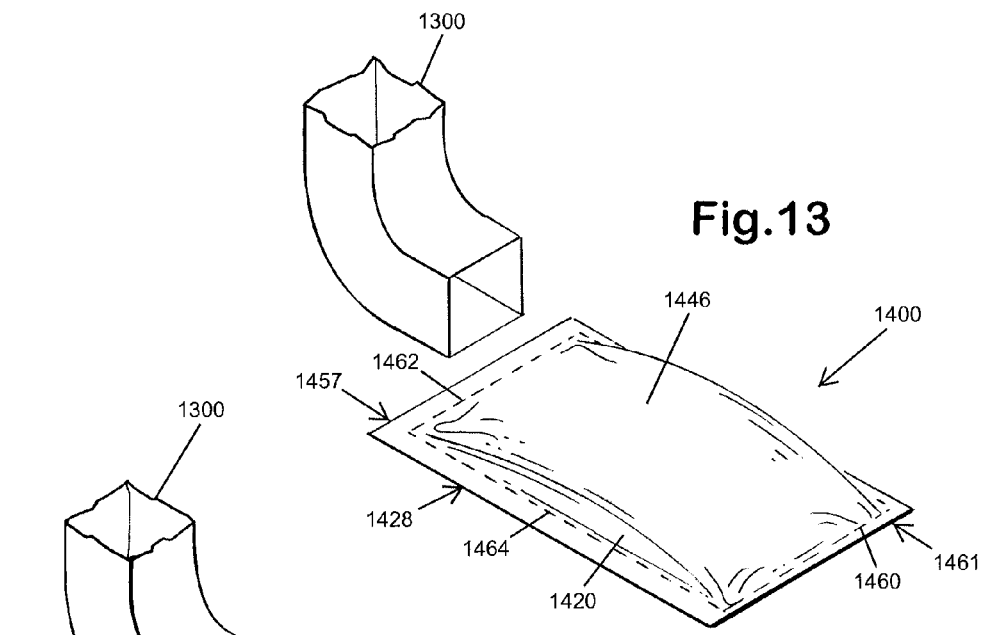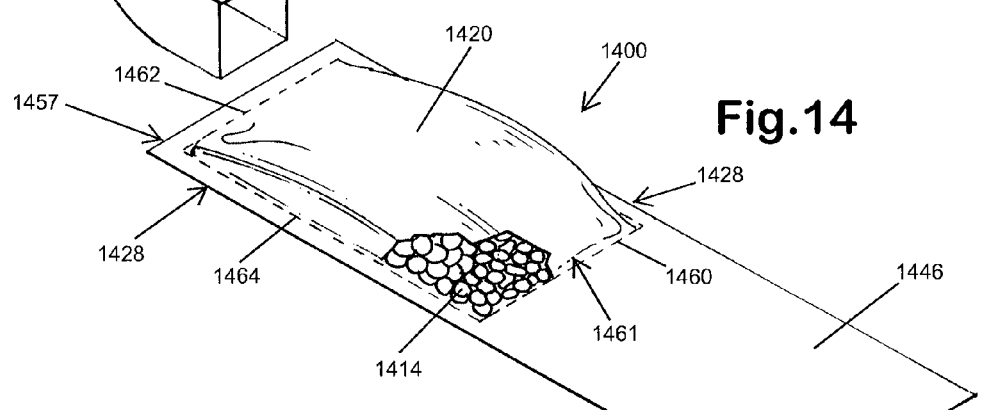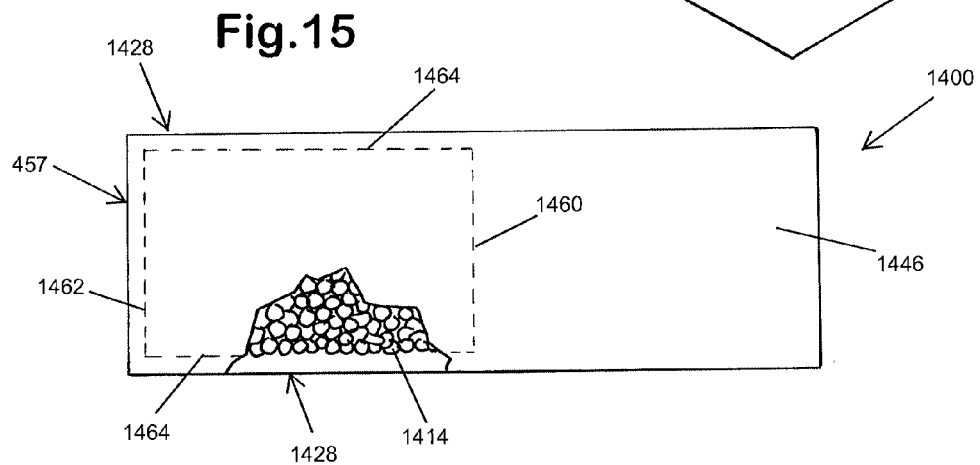

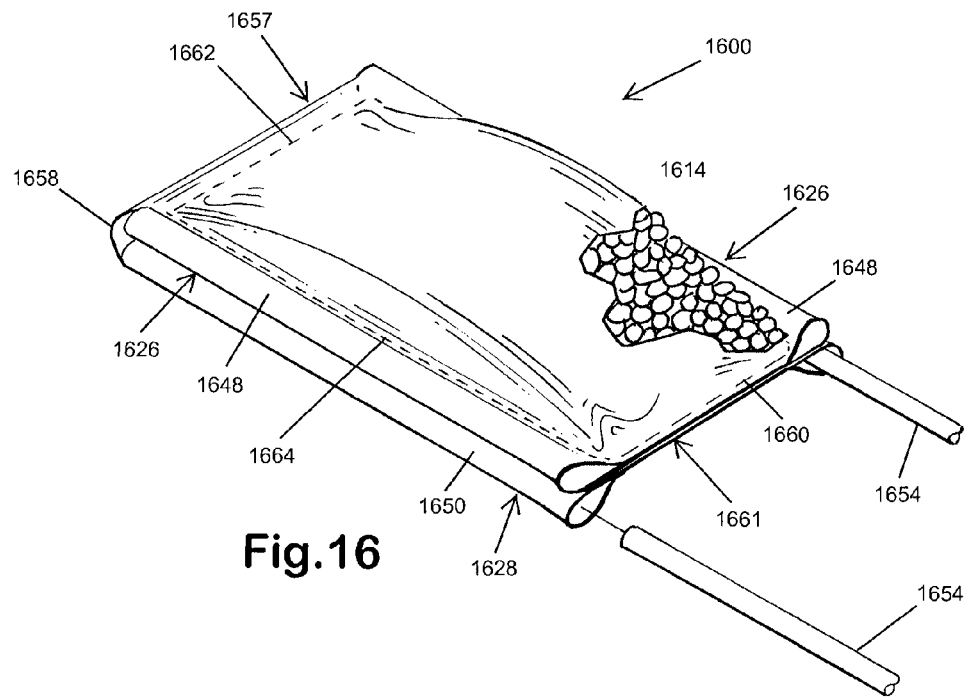
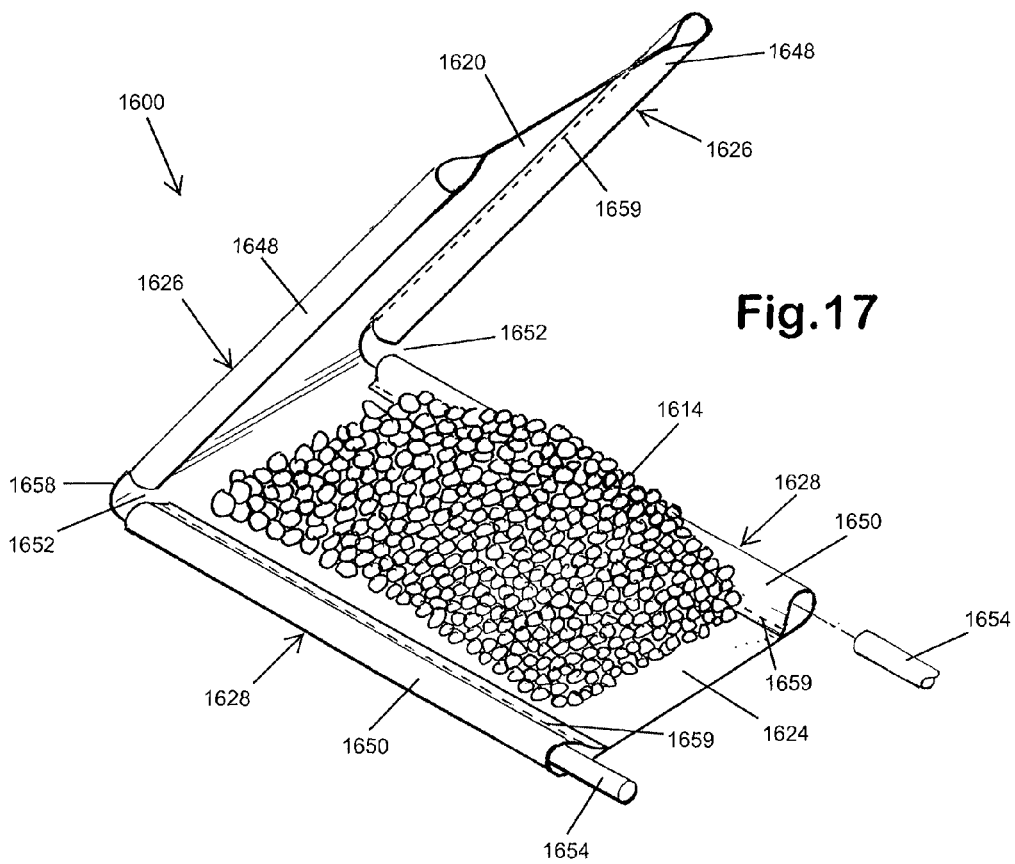

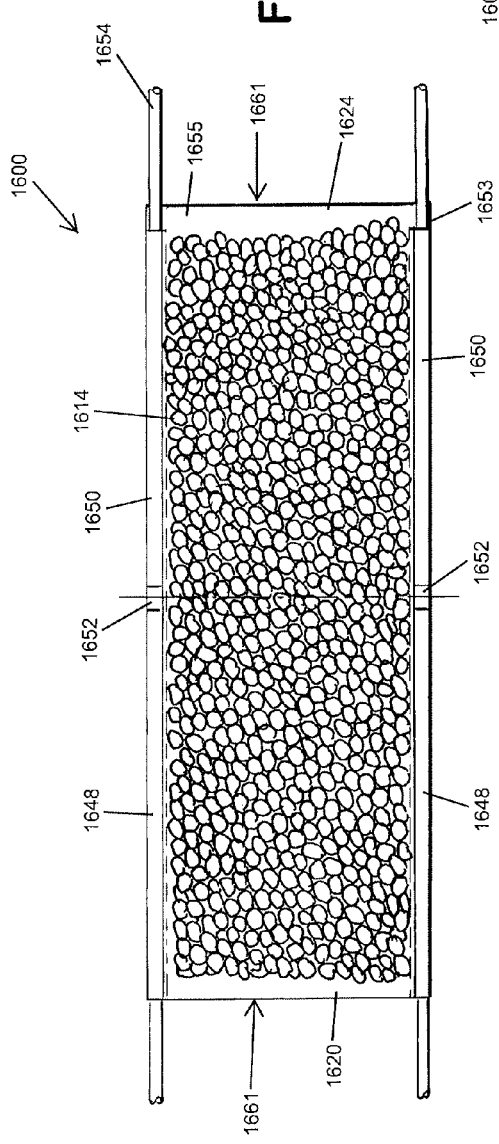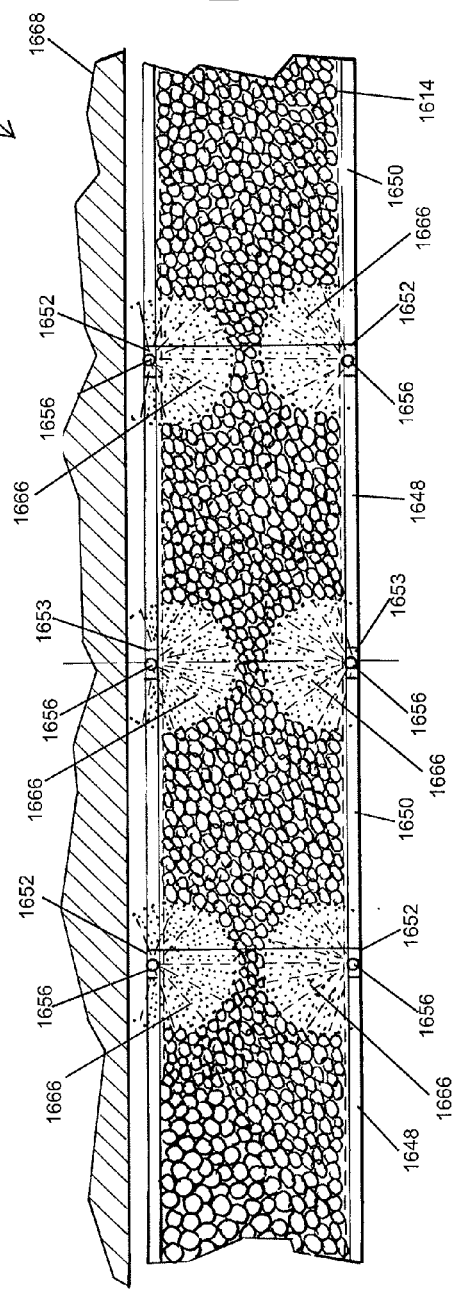

METHODS FOR CONTROLLING WEEDS AND WATER USING A BAG FILLED WITH LANDSCAPING MATERIAL

CROSS-REFERENCE TO RELATED APPLICATIONS

This application is a continuation-in-part application of U.S. patent application Ser. No. 13/959,204, filed Aug. 5, 2013, which is a continuation-in-part application of U.S. patent application Ser. No. 12/795,841, filed Jun. 8, 2010, now U.S. Pat. No. 8,522,476, all of which are incorporated herein by reference.

FIELD OF THE INVENTION

This invention generally relates to a bag for packaging landscaping material, and more particularly to methods for using the bag for weed suppression, pest control, and water control.

BACKGROUND OF THE INVENTION

In a planting bed for flowers and/or vegetables, a ground cover material, including mulches, rock material, composted soil (garden soil or potting soil), and ground synthetic particles, is often spread on top of the soil among the flowering plants and/or the vegetables plants. The ground cover material offers several advantages. The ground cover can be selected to maintain soil moisture or to inhibit soil compaction. In the case of flower beds, the ground cover material can be selected to create a pleasing aesthetic appearance to show off the flowers.

In order to lower the maintenance required for planting beds, particularly to inhibit the growth of weeds in the planting beds, a separate weed suppression material is often laid on top of the soil and under the ground cover.

In planting individual plants, such as flowers and/or vegetables, in a planting bed, the soil of the planting bed often needs amendment by the addition of a top layer of enriched composted soil. In addition, weeds in the planting bed should be controlled as the flowers and/or vegetables mature. Further, moisture should be retained in the soil of the planting bed. Therefore, a need exists for a simple method for planting individual plants, such as flowers and/or vegetables, in a planting bed that addresses the need for soil amendment, weed control in the planting bed and moisture retention.

Organic materials and mulches located adjacent the foundation of a building create a risk of insect intrusion and of water damage. Consequently, a need exists to easily create a buffer zone of rock material along the perimeter of the foundation of the building to inhibit insect intrusion and control water damage.

Downspouts from the gutters of a building create the potential for erosion at the site where the downspout discharges water onto the landscape around the building. Therefore, a need exists for erosion control at the discharge point of the building downspouts.

SUMMARY OF THE INVENTION

The present invention addresses both the need for a ground cover material and the need for a weed suppression material for a planting bed. Particularly, the present invention comprises a bag constructed of a weed suppression material for packaging a ground cover material. When the bag of the present invention is in its closed configuration, the bag serves as a container for shipping, handling, and storage of the ground cover material. When installing the ground cover material in the planting bed, the bag of the present invention is opened and unfolded, and the ground cover material within the bag is spread over the opened and unfolded bag. Consequently, the bag serves as a layer of weed suppression material on top of the underlying soil and beneath the ground cover.

The ground cover material that may be used in connection with the bag of the present invention may include mulches, such as pine straw, chipped wood bark, grain straws, shredded wood materials, or other mulches known to those of ordinary skill in the landscaping art. The ground cover may also include rock material, including sand, crushed stone, gravel, pea gravel, graded stone, shale, or other rock materials known to those of ordinary skill in the landscaping art. The ground cover may also include ground synthetic particles, such as ground rubber particles and ground plastic particles. The ground cover may also include composted soil.

The weed suppression material for the bag of the present invention may be a sheet of perforated plastic, biodegradable/compostable plastic film, paper, cardboard or cloth fabric. For most planting bed applications, the weed suppression material should be porous in order to allow water and air to pass through the weed suppression material to the roots of the plants in the underlying soil. The bag of the present invention may be constructed with an impervious temporary outer coating or an impervious internal liner to ensure integrity of the bag during shipping, handling, and storage. The temporary coating or liner dissolves when the bag comes in contact with moist soil, or the temporary liner is manually removed when the bag is opened. Further, the weed suppression material of the bag may be biodegradable within a 3 to 24 month period of time to ensure suppression of weeds during the growing season and to ensure that there is no buildup of the weed suppression material in the planting bed from growing season to growing season. The weed suppression material of the bag may also be compostable. The weed suppression material of the bag may be colored on the inside to match the color of the ground cover packaged in the bag so that when in place, the bag, underlying the ground cover material, will not be obtrusive in the planting bed. The weed suppression material comprising the bag may also be coated or impregnated with an additive including fertilizer, pesticide, insecticide, freeze-dried, or beneficial microbes for release into the underlying soil. Because the area of the unfolded bag is a known parameter, the impregnated bag provides an accurate dose of fertilizer, pesticide, insecticide, herbicide, or beneficial microbes to the underlying soil. Further, the weed suppression material comprising the bag may also be coated with or impregnated with an antimicrobial so that the bag does not mildew or mold during shipping, handling or storage.

In applications where the ground cover is spread over a large area without planting beds, the weed suppression material may be impervious to both air and water to ensure total weed control by depriving the weeds in the underlying soil of moisture and air. In such circumstances, the impervious weed suppression material may also be used to direct the flow of water toward drainage facilities or toward adjacent plant beds to increase the water available for such adjacent plant beds. Such an impervious weed suppression material may include, among other materials, a plastic film or a coated paper laminate.

The bag constructed of weed suppression material in accordance with the present invention has indicia on its outer surface indicating where and how the bag should be opened. Particularly, the indicia may comprise bonded seams (glued or hot melted), sewn seams, tear strips, perforations, or printed cut lines to facilitate opening and use of the bag as a weed suppression material. In one embodiment of the bag in accordance with the present invention, the bag may have bonded seams (glued or hot melted), sewn seams, tear strips, perforations, or printed cut lines arranged in the form of a capital "I", with the leg of the "I" running along the center of the length of the bag and with the top and bottom bars of the "I" running along the end edges of the bag. In a second embodiment of the bag in accordance with the present invention, the bag may have bonded seams (glued or hot melted), sewn seams, tear strips, perforations, or printed cut lines arranged in the form of a capital "I", with the leg of the "I" running along the center of the width of the bag and with the top and bottom bars of the "I" running along the side edges of the bag. In a third embodiment of the bag in accordance with the present invention, the bag may have bonded seams (glued or hot melted), sewn seams, tear strips, perforations, or printed cut lines on both end edges and on one of the side edges of the bag. In a third embodiment of the bag in accordance with the present invention, the bag may have bonded seams (glued or hot melted), sewn seams, tear strips, perforations, or printed cut lines on both side edges and on one of the end edges of the bag.

In use, the bag of the present invention containing the ground cover (mulch, rock, composted soil, or ground synthetic particles) is laid on the exposed soil adjacent the plants. The bag is then opened by means of indicia, such as bonded seams (glued or hot melted), sewn seams, tear strips, perforations, or printed cut lines. Once the bag has been opened, the bag is unfolded around the plants in the planting bed. Holes are cut or torn in the weed suppression material to accommodate the plants in the planting bed. The installation is completed by spreading the ground cover over the exposed portions of the unfolded bag. Alternatively, the bag and groundcover may be installed before plants are installed in the planting bed. In that circumstance, holes are cut or torn in the bag after installation of the bag and ground cover, and the plants are inserted through the holes in the bag into the underlying soil. Where enriched composted soil, such as garden soil is used as ground cover, the bag is opened and placed flat over the underlying soil. The composted soil in the bag is then spread over the open bag. The plants are then planted through a hole in the open bag and grow through the composted soil on top of the bag while the weeds in the underlying soil are suppressed.

The relationship between the size of the bag and the amount of ground cover contained in the bag provides a measure for the proper installation of the ground cover to the proper depth. In other words, the amount of ground cover included in the bag is just the right amount to cover the bag to the proper depth when the bag is unfolded. In order to accommodate the volume of ground cover material in the bag, the bag may also include one or more extra panels attached adjacent the bonded seams (glued or hot melted), sewn seams, tear strips, perforations, or printed cut lines so that, when the bag is unfolded with the extra panels, additional area of weed suppression material is available to accommodate the volume of ground cover material in the bag.

Further, the present invention contemplates a bag that is constructed of water permeable, biodegradable material and that is filled with planting material including but not limited to enriched composted soil, mulches (organic and inorganic), soil amendment products, or mixtures thereof. Such a bag enables a method of planting individual plants, such as flowers and/or vegetables, in a planting bed while at the same time amending the soil of the planting bed, controlling weeds in the planting bed, and retaining moisture in the planting bed. The bag is laid out on the planting bed, opened along indicia representing means for opening the bag, and unfolded to a flat configuration. Once unfolded, the enriched soil is spread out to cover the water permeable, biodegradable bag. Once the bag has been opened, laid flat, and covered with the enriched soil, individual openings are made in the enriched soil, the bag, and the underlying soil of the planting bed. Individual plants are inserted into the openings and therefore in contact with the overlying enriched soil, the water permeable biodegradable bag, and the underlying soil of the planting bed.

The present invention also contemplates a foundation buffer bag that is constructed of a water impermeable, non-degradable material and that is filled with a ground cover such as a rock material or synthetic particles. Such a buffer bag enables a method of establishing a protective buffer zone adjacent the foundation of a building to lower the risk of insect intrusion and water damage. The bag is dimensioned to coincide with the width of the buffer zone. The buffer bag is laid out adjacent the foundation of the building, opened along indicia comprising means for opening the buffer bag, and unfolded to a flat configuration adjacent the building foundation. Once unfolded, the ground cover in the buffer bag is spread out to cover the flat impermeable, non-degradable bag except for a segment at one end. The next buffer bag is laid out in the same fashion and overlaps the uncovered segment of the first buffer bag. The ground cover in the second buffer bag is then spread out to cover the overlap leaving another uncovered segment at the opposite end to accommodate the third buffer bag, and so on to create the buffer zone. Alternatively, the foundation buffer bag may be configured as a buffer spray bag that includes sleeves along the side edges of the front panel and along the side edges of the back panel. Once the spray bag is unfolded, the front panel sleeves and the back panel sleeves form sectioned sleeves along the side edges of the unfolded spray bag with gaps between the front panel sleeves and the back panel sleeves. Tubing may then be inserted into the sleeves along the edges of the bag, and emitters or spray heads may be connected to the tubes at the gaps. The emitters or spray heads are then used to spray pesticides onto the ground cover thereby creating a pesticide treated a buffer zone adjacent the foundation of the building. Alternatively, the tubes may be inserted into the sleeves of the bag prior to shipment.

The present invention also contemplates a downspout bag that is constructed of a water permeable, non-degradable material and that is filled with a ground cover such as rock material or synthetic particles. Such a downspout bag enables a method of controlling erosion at the point where a downspout or other conduit discharges water onto the surrounding landscape or where other water runoff occurs. The water permeable, non-degradable downspout bag is laid out so that the downspout discharges water directly onto the front panel of the bag. Because the downspout bag is permeable, the water passes into the downspout bag and is dispersed through the bottom panel of the downspout bag into the surrounding soil. The ground cover in the downspout bag provides structure for the downspout bag and keeps the back panel of the downspout bag fully and frictionally engaged with the soil below. The back panel of the bag may be less water permeable than front panel in order to partially direct water away from the underlying soil. Alternatively, the water permeable, non-degradable downspout bag may be opened along indicia comprising means for opening the downspout bag and unfolded to a flat configuration under the downspout. The ground cover is then spread over the flat downspout bag so that the water discharged from the downspout impinges directly on the ground cover. The ground cover holds the water permeable, non-degradable material of the downspout bag securely against the underlying soil to frictionally engage and hold the soil in place. In a further alternative, the water permeable, non-degradable downspout bag may include an additional flap that extends from one end of the downspout bag to provide a spillway for excess water that is not retained by the ground cover or dispersed through the back panel of the downspout bag into the surrounding soil. The back panel of the bag and the additional flap may be less water permeable than the front panel of the bag in order to partially direct water away from the area surrounding the bag and the unfolded flap.

Further objects, features and advantages will become apparent upon consideration of the following detailed description of the invention when taken in conjunction with the drawings and the appended claims.

BRIEF DESCRIPTION OF THE DRAWINGS

FIG. 11 is a section view of planting bed soil, of a weed suppression material of the bags of FIGS. 1-10 opened and unfolded on top of the soil, and ground cover on top of the weed suppression material all in accordance with the present invention.

FIG. 12 is a section view of the planting bed soil, of a multilayer weed suppression material of the bags of FIGS. 1-10 opened and unfolded on top of the soil, and ground cover on top of the weed suppression material all in accordance with the present invention.

FIG. 13 is a perspective view of a downspout bag.

FIG. 14 is a perspective view of a downspout bag with a flap forming a spillway.

FIG. 15 is a plan view of the downspout bag with the flap forming a spillway.

FIG. 16 is a perspective view of a spray bag with edge sleeves in a closed configuration.

FIG. 17 is a perspective view of the spray bag with edge sleeves in a partially opened configuration.

FIG. 18 is a plan view of the spray bag with sectioned edge sleeves and with tubing installed.

FIG. 19 is a plan view of the spray bag with sectioned edge sleeves and with tubing and emitters installed.

DETAILED DESCRIPTION OF THE PREFERRED EMBODIMENTS

Figure 1:
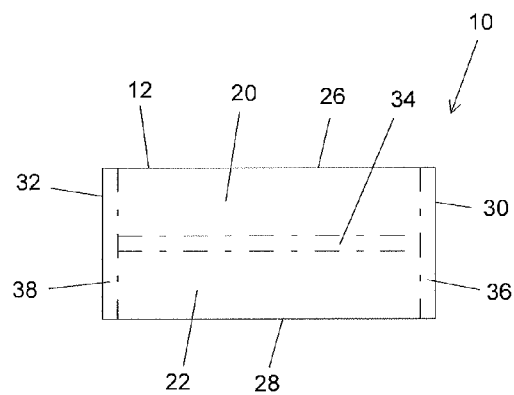
FIG. 1 is a top plan view of a first embodiment of an unopened bag with bonded seams (glued or hot melted), sewn seams, tear strips, perforations, or printed cut lines in an "I" shape in accordance with the present invention.
Figure 2:
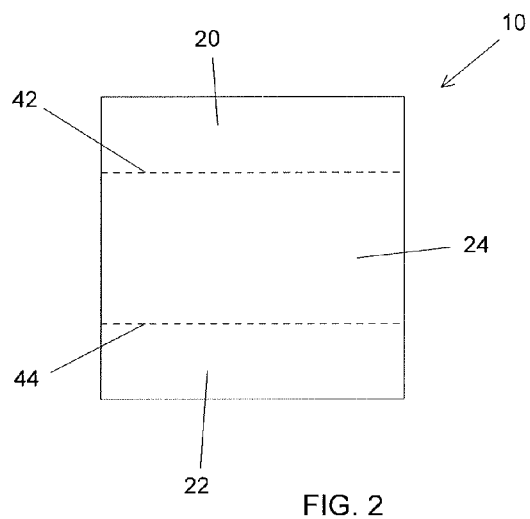
FIG. 2 is a top plan view of the bag of FIG. 1 opened and unfolded in accordance with the present invention.

Referring now to the drawings, a first embodiment of a bag 10, constructed of weed suppression material 12 in accordance with the present invention, is illustrated FIGS. 1-2. FIG. 1 shows the bag 10 in its closed configuration. FIG. 2 shows the bag 10 in its open configuration. The bag 10 is formed of a weed suppression material 12. The weed suppression material 12 for the bag 10 may be a sheet of perforated plastic, biodegradable/compostable plastic film, paper, cardboard, or cloth fabric (woven or nonwoven). For most planting bed applications, the weed suppression material 12 may be a layer 13 (FIG. 11) of porous material in order to allow water and air to pass through the weed suppression material 12 to the underlying soil 18 (FIG. 11). In practice, the porous layer 13 may be implemented by three layers of wet strength Kraft paper. The number and thickness of individual layers comprising porous layer 13 may be adjusted to meet the strict requirements of shipping, handling and storage on one hand, and proper porosity for use as a weed suppression material.

The bag 10 of the present invention may also be constructed with an impervious temporary outer coating (not shown) or an impervious temporary internal liner 15 (FIG. 12) to ensure integrity of the bag 10 during shipping, handling, and storage. The temporary impervious coating or liner 15 dissolves when the weed suppression material 12 bag comes in contact with moist soil 18, or the temporary impervious liner 15 is manually removed when the bag is opened. Further, the weed suppression material 12 of the bag 10 may be biodegradable within a 3 to 24 month period of time to ensure suppression of weeds during the growing season and to ensure that the weed suppression material 12 does not build up in the planting bed from growing season to growing season. The weed suppression material 12 of the bag 10 may also be compostable.

The weed suppression material 12 of the bag 10 may be colored on the inside of the bag 10 to match the color of the ground cover 14 (FIGS. 11 and 12) packaged in the bag 10 so that when in place, the bag 10, underlying the ground cover material, will not be obtrusive in the planting bed. The weed suppression material 12 comprising the bag 10 may also be impregnated with fertilizer, pesticide, insecticide, herbicide, or beneficial microbes for release into the underlying soil. Boric acid may be coated onto the weed suppression material 12 to reduce flammability and to provide an insecticide. Further, the weed suppression material comprising the bag may also be coated with or impregnated with an antimicrobial so that the bag does not mildew or mold during shipping, handling, and storage. Because the area of the unfolded bag 10 (FIG. 2) is a known parameter, the impregnated bag 10 provides an accurate dose of fertilizer, pesticide, insecticide, herbicide, or beneficial microbes to the underlying soil. Likewise, because the area of the unfolded bag is known, the amount of ground cover contained in the bag can be measured to ensure that when ground cover is spread on the open bag, the ground cover is at the correct depth.

As previously indicated, where the ground cover is spread over a large area without planting beds, the weed suppression material 12 in the bag 10 may be impervious to both air and water to ensure total weed control by depriving the weeds in the underlying soil of moisture and air. In such circumstances, the impervious weed suppression material 12 may also be used to direct the flow of water toward drainage facilities or toward adjacent plant beds to increase the water available for such adjacent planting beds. Such an impervious weed suppression material may include, among other materials, a plastic film or a coated paper laminate. The plastic film or the coated paper laminate may be either permanent or biodegradable/compostable depending on the application. The plastic film or the coated paper laminate may also be colored to blend with the color of the ground cover material.

With continuing reference to FIG. 1, the bag 10 comprises a first front panel 20, a second front panel 22, and a back panel 24. The first front panel 20, the second front panel 22, and the back panel 24 are all connected together at a first side edge 26, a second side edge 28, a first end edge 30, and a second end edge 32 to form the bag 10 for packaging the ground cover material 14 during shipping, handling, and storage. The bag 10 further has a center tear strip or indicia 34, a first end tear strip 36, and a second end tear strip 38. (The terms "tear strip" or "indicia" as used hereinafter should be understood to refer to bonded seams (glued or hot melted), sewn seams, tear strips, perforations, or printed cut lines.) The center tear strip 34 interconnects the first front panel 20 and the second front panel 22. The first end tear strip 36 connects the edges of the first front panel 20, the second front panel 22, and the back panel 24 along the first end edge 30. The second end tear strip 38 connects the edges of the first front panel 20, the second front panel 22, and the back panel 24 along the second end edge 32.

In order to use the bag 10 as a weed suppression material, the center tear strip 34, the first end tear strip 36, and the second end tear strip 38 are removed from the bag 10. With the tear strips 34, 36, and 38 removed, the bag 10 is then unfolded as shown in FIG. 2. A first side fold line 42 corresponds to the first side edge 26 of the bag 10 (FIG. 1), and a second side fold line 44 corresponds to the second side edge 28 of the bag 10 (FIG. 1). Once the bag 10 has been unfolded as shown in FIG. 2, the ground cover material 14 is spread over the bag 10 in its open and unfolded configuration.

Although the bag 10 has been described in connection with the use of tear strips 34, 36, and 38, as indicated above, other opening means, such as bonded seams (glued or hot melted), sewn seams, perforations, or printed cut lines may be used in connection with the present invention. Particularly, the printed cut lines direct the user to those places on the bag that should be cut in order to open the bag 10 to its open and unfolded configuration shown in FIG. 2. Instead of printed cut lines, perforations may be provided to facilitate the opening of the bag 10 along the edges and center. In another embodiment, instead of a tear strip, the edges 30 and 32 may be sealed by a standard sewn closure which is easily opened by pulling on the thread of the sewn closure. Also, the center tear strip 34 may be accessible from the inside of the bag once the edges have been opened by removing the tear strips 36 and 38.

Figure 3:
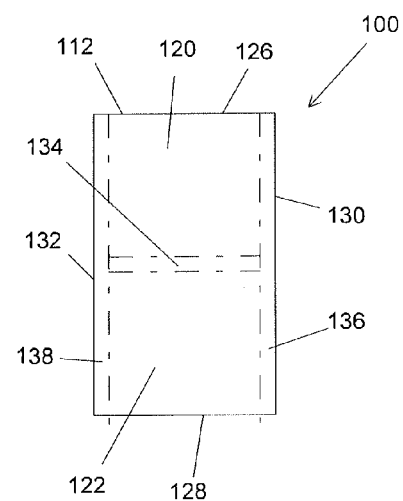
FIG. 3 is a top plan view of a second embodiment of an unopened bag with bonded seams (glued or hot melted), sewn seams, tear strips, perforations, or printed cut lines in an "I" shape in accordance with the present invention.
Figure 4:
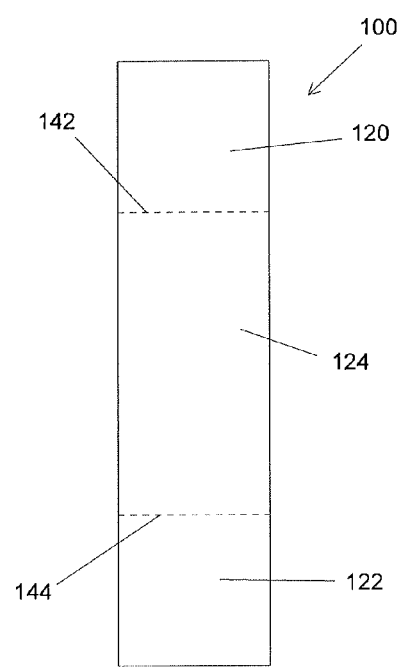
FIG. 4 is a top plan view of the bag of FIG. 3 opened and unfolded in accordance with the present invention.

FIGS. 3 and 4 show a second embodiment of a bag 100 of the present invention. The bag 100 comprises a first front panel 120, a second front panel 122, and a back panel 124. The first front panel 120, the second front panel 122, and the back panel 124 are all connected together at a first end edge 126, a second end edge 128, a first side edge 130, and a second side edge 132 to form the bag 100 for packaging the ground cover material during shipping, handling, and storage. The bag 100 further has a center tear strip 134, a first side tear strip 136, and a second side tear strip 138. The center tear strip 134 interconnects the first front panel 120 and the second front panel 122. The first side tear strip 136 connects the edges of the first front panel 120, the second front panel 122, and the back panel 124 along the first side edge 130. The second side tear strip 138 connects the edges of the first front panel 120, the second front panel 122, and the back panel 124 along the second side edge 132.

In order to use the bag 100 as a weed suppression material, the center tear strip 134, the first side tear strip 136, and the second side tear strip 138 are removed from the bag 100. With the tear strips 134, 136, and 138 removed, the bag 100 is then unfolded as shown in FIG. 4. A first end fold line 142 corresponds to the first end edge 126 of the bag 100, and a second end fold line 144 corresponds to the second end edge 128 of the bag 100. Once the bag 100 has been unfolded as shown in FIG. 4, the ground cover material 14 contained within the bag 100 is spread over the bag 100 in its open and unfolded configuration. Further, as previously stated, other opening indicia, such as bonded seams (glued or hot melted), sewn seams, perforations, or printed cut lines, can be substituted for the tear strips 134, 136, and 138.

Figure 5:
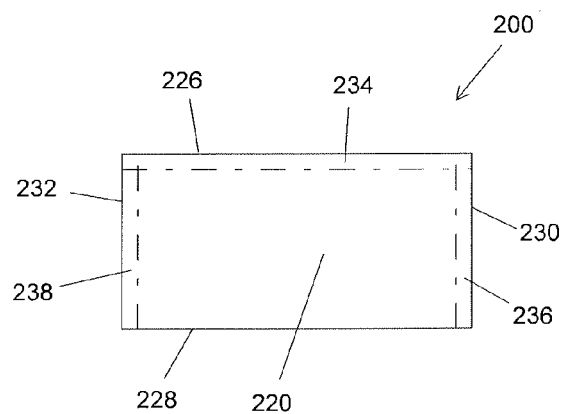
FIG. 5 is a top plan view of a third embodiment of an unopened bag with sewn bonded seams (glued or hot melted), seams, tear strips, perforations, or printed cut lines along two end edges and along one side edge in accordance with the present invention.
Figure 6:
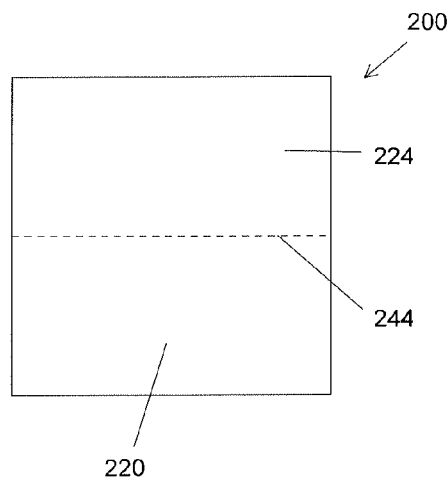
FIG. 6 is a top plan view of the bag of FIG. 5 opened and unfolded in accordance with the present invention.

FIGS. 5 and 6 show a third embodiment of a bag 200 of the present invention. The bag 200 comprises a front panel 220 and a back panel 224. The front panel 120 and the back panel 224 are connected together at a first side edge 226, a second side edge 228, a first end edge 230, and a second end edge 232 to form the bag 200 for packaging the ground cover material during shipping, handling, and storage. The bag 200 further has a side tear strip 234, a first end tear strip 236, and a second end tear strip 238. The side tear strip 234 interconnects the front panel 220 and the back panel 224. The first end tear strip 236 interconnects the edges of the front panel 220 and the back panel 224 along the first end edge 230. The second end tear strip 238 interconnects the edges of the front panel 220 and the back panel 224 along the second end edge 232.

In order to use the bag 200 as a weed suppression material, the side tear strip 234, the first end tear strip 236, and the second end tear strip 238 are removed from the bag 200. With the tear strips 234, 236, and 238 removed, the bag 200 is then unfolded as shown in FIG. 6. A side fold line 244 corresponds to the second side edge 228 of the bag 200 (FIG. 5). Once the bag 200 has been unfolded as shown in FIG. 6, the ground cover material 14 contained within the bag 200 is spread over the bag 200 in its open and unfolded configuration. Further, as previously stated, other opening indicia, such as bonded seams (glued or hot melted), sewn seams, perforations, printed cut lines, can be substituted for the tear strips 234, 236, and 238.

Figure 7:
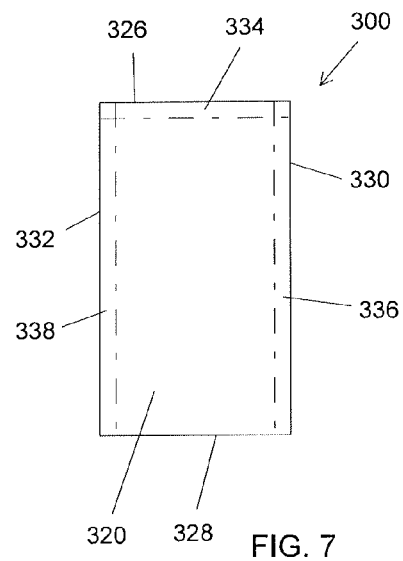
FIG. 7 is a top plan view of a fourth embodiment of an unopened bag with sewn bonded seams (glued or hot melted), seams, tear strips, perforations, or printed cut lines along two sides edges and along one end edge in accordance with the present invention.
Figure 8:
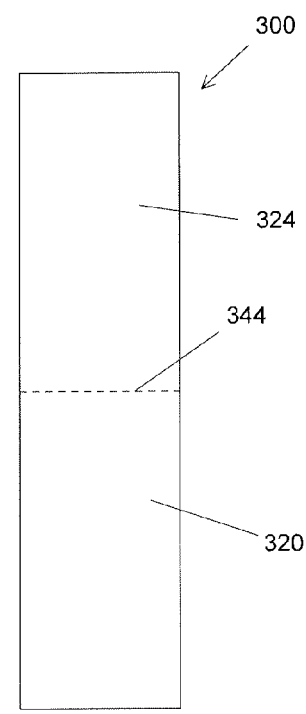
FIG. 8 is a top plan view of the bag of FIG. 7 opened and unfolded in accordance with the present invention.

FIGS. 7 and 8 show a fourth embodiment of a bag 300 of the present invention. The bag 300 comprises a front panel 320 and a back panel 324. The front panel 320 and the back panel 324 are connected together at a first end edge 326, a second end edge 328, a first side edge 330, and a second side edge 332 to form the bag 300 for packaging the ground cover material during shipping, handling, and storage. The bag 300 further has an end tear strip 334, a first side tear strip 336, and a second side tear strip 338. The end tear strip 334 interconnects the front panel 320 and the back panel 324. The first side tear strip 336 interconnects the edges of the front panel 320 and the back panel 324 along the first side edge 330. The second side tear strip 338 interconnects the edges of the front panel 320 and the back panel 324 along the second side edge 332.

In order to use the bag 300 as a weed suppression material, the end tear strip 334, the first side tear strip 336, and the second side tear strip 338 are removed from the bag 300. With the tear strips 334, 336, and 338 removed, the bag 300 is then unfolded as shown in FIG. 8. A side fold line 344 corresponds to the second end edge 328 of the bag 300 (FIG. 7). Once the bag 300 has been unfolded as shown in FIG. 8, the ground cover material 14 contained within the bag 300 is spread over the bag 300 in its open and unfolded configuration. Further, as previously stated, other opening indicia, such as bonded seams (glued or hot melted), sewn seams, perforations, or printed cut lines, can be substituted for the tear strips 334, 336, and 338.

Figure 9:
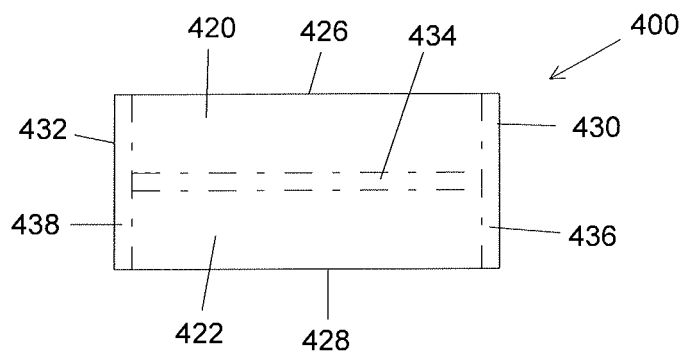
FIG. 9 is a top plan view of a fifth embodiment of an unopened bag with bonded seams (glued or hot melted), sewn seams, tear strips, perforations, or printed cut lines in an "I" shape in accordance with the present invention.
Figure 10:
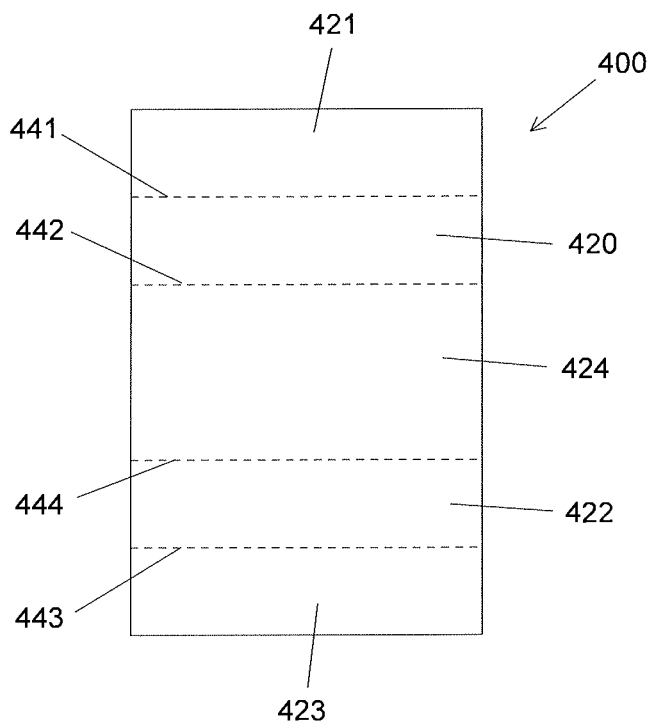
FIG. 10 is a top plan view of the bag of FIG. 9 opened and unfolded and including extra panels in accordance with the present invention.

FIGS. 9 and 10 show a fifth embodiment of a bag 400 of the present invention. The bag 400 comprises a first front panel 420 with an extra underlying panel 421, a second front panel 422 with an extra underlying panel 423, and a back panel 424. The first front panel 420 with its extra underlying panel 421, the second front panel 422 with its extra underlying panel 423, and the back panel 24 are all connected together at a first side edge 426, a second side edge 428, a first end edge 430, and a second end edge 432 to form the bag 400 for packaging the ground cover material during shipping, handling, and storage. The bag 400 further has a center tear strip 434, a first end tear strip 436, and a second end tear strip 438. The center tear strip 434 interconnects the first front panel 420 and the second front panel 422. The first end tear strip 436 interconnects the edges of the first front panel 420, the second front panel 422, and the back panel 424 along the first end edge 430. The second end tear strip 438 interconnects the edges of the first front panel 420, the second front panel 422, and the back panel 424 along the second end edge 432. The underlying panel 421 is hinged to the first front panel 420 adjacent the center tear strip 434 and is folded back underneath the first front panel 420 inside of the bag 400. Likewise, the underlying panel 423 is hinged to the second front panel 422 adjacent the center tear strip 434 and is folded back underneath the second front panel 422 inside of the bag 400. The extra underlying panel 421 and the extra underlying panel 423 may be placed above the first front panel 420 and the second front panel 422, respectively, instead of underlying those front panels 420 and 422.

In order to use the bag 400 as a weed suppression material, the center tear strip 434, the first end tear strip 436, and the second end tear strip 438 are removed from the bag 400. With the tear strips 434, 436, and 438 removed, the bag 400 is then unfolded as shown in FIG. 10. A first side fold line 442 corresponds to the first side edge 426 of the bag 10. A second side fold line 444 corresponds to the second side edge 428 of the bag 400. A third fold line 441 corresponds to the hinged connection between the first front panel 420 and its underlying panel 421. A fourth fold line 443 corresponds to the hinged connection between the second front panel 422 and its underlying panel 423. The extra underlying panels 421 and 423 provide extra weed suppression material to accommodate the volume of ground cover material contained within the bag 400. Once the bag 400 has been unfolded as shown in FIG. 10, the ground cover material 14 contained within the bag 400 is spread over the bag 400 in its open and unfolded configuration with its extra area provided by the extra panels 421 and 423. Further, as previously stated, other opening indicia, such as bonded seams (glued or hot melted), sewn seams, perforations, or printed cut lines, can be substituted for the tear strips 434, 436, and 438.

Preferably, the bags 10, 100, 200, 300 and 400 are flat tube bags that are sewn at the edges and along one side to provide the opening lines. Other types of bags, such as gusset bags, may be used in connection with the invention.

One construction of bags in accordance with the present invention comprises a tube bag made of three layers of 50 pound basis weight, wet strength Kraft paper. The bags were installed in planting beds with pine bark mulch. Over a seven-month period, the bags had begun to degrade in response to environmental conditions. The bags, however, continued to suppress weed growth at approximately a 90% reduction compared to planting beds without the weed suppression material.

The construction of bag 10 or 200 is suitable for use with a method for planting individual plants, such as flowers and/or vegetables in a planting bed with existing soil. Particularly, the bag 10 or 200 is constructed of water permeable, biodegradable material, and the bag 10 or 200 is filled with ground cover including but not limited to enriched composted soil, mulches (organic and inorganic), soil amendment products, or mixtures thereof. The bag 10 or 200 is laid out on the planting bed, opened along indicia 34, 36, and 38 for the bag 10 or along indicia 234, 236, and 238 for the bag 200. Once opened the bag 10 or 200 is unfolded to a flat configuration, the ground cover in the bag 10 or 200 is spread out to cover the water permeable, biodegradable material of the bag 10 or 200. In order to facilitate the spreading of the ground cover over the water permeable, biodegradable material of the bag 10 or 200, a lip may optionally be created along the edge of the flattened bag by folding and securing the material to itself along the indicia. The lip provides a barrier to retain the ground cover from spreading beyond the edge of the flattened bag. Once the bag 10 or 200 has been opened, laid flat, and covered with the ground cover, individual openings are made through the ground cover, through the water permeable, biodegradable material of the bag 10 or 200, and into the underlying soil of the planting bed. Individual plants are then inserted into each of the openings. Each individual plant therefore is in contact with the overlying ground cover, the water permeable, biodegradable material of the bag 10 or 200, and the underlying soil of the planting bed. The method employing the bag 10 or 200 for planting individual plants in the planting bed offers several advantages. First, the ground cover in the bag 10 or 200 amends the soil of the planting bed and delivers nutrients to the individual plants. Second, the water permeable, biodegradable material of the bag 10 or 200 creates a weed barrier between the individual plants. Third, the water permeable, biodegradable material of the bag 10 or 200 acts as a mulch to retain moisture in the soil of the planting bed. Fourth, the water permeable, biodegradable material of the bag 10 or 20 degrades over the course of a growing season so that the bag material can simply be tilled into the soil of the planting bed the following year thereby eliminating the need to dispose of the bag 10 or 200.

The construction of bag 100 or 300 constitutes a foundation buffer bag and is suitable for use with a method for creating a protective buffer zone about 12-18 inches in width around the foundation of a building to inhibit the intrusion of insects and to protect against water damage. The buffer bag 100 or 300 is constructed of a water impermeable, non-degradable material, and the buffer bag 100 or 300 is filled with a ground cover such as rock material or synthetic particles. In the first step of the method, organic material is removed from the buffer zone around the foundation of the building. The grade of the buffer zone should slope away from the foundation. The buffer bag 100 or 300 is dimensioned to coincide with the width of the buffer zone. After the buffer zone has been cleared of organic material and graded, the buffer bag 100 or 300 is laid in the buffer zone adjacent the foundation of the building, opened along indicia 134, 136, and 138 for the buffer bag 100 and along indicia 334, 336, and 338 for the buffer bag 300, and unfolded to a flat configuration covering the buffer zone adjacent the building foundation. The buffer bag 100 or 300 may optionally have a lip as previously described with respect to the bag 10 or 200 used for planting individual plants in a planting bed. Once unfolded, the ground cover in the buffer bag 100 or 300 is spread out to cover the flat impermeable, non-degradable material of the buffer bag 100 or 300 except for a segment of the impermeable, nondegradable material at one end of the bag 100 or 300. The second buffer bag is laid out in the same fashion and overlaps the uncovered segment of the first buffer bag. The ground cover in the second buffer bag is then spread out to cover the overlap leaving another uncovered segment at the opposite end of the second buffer bag to accommodate the third buffer bag, and so on until the buffer zone is covered with ground cover. The method employing the buffer bag 100 or 300 for creating the protective buffer zone around the foundation of the building offers several advantages. First, the ground cover, such as rock material and synthetic particles, in the protective buffer zone inhibits ingress of insects to the foundation of the building. Second, the ground cover in the bag can be selected for size, shape, and coloration in order to provide a desired aesthetic appearance for the buffer zone. Third, because the material of the bag is water permeable and non-degradable the flattened bag can serve as flashing to direct water away from the foundation of the building.

Turning to FIGS. 16-19, a buffer spray bag 1600 is used to create a chemical pesticide barrier around the foundation of a building. Particularly, the spray bag 1600 comprises a front panel 1620 and a back panel 1624. The front panel 1620 and the back panel 1624 are formed of a continuous web of water impermeable, non-degradable material with a fold 1658 at fold end 1657. At the opposite opening end 1661, the front panel 1620 and the back panel 1624 are coterminous. The front panel 1620 has a pair of front panel sleeves 1648 connected along side edges 1626, and the back panel 1624 has a pair of back panel sleeves 1650 connected along side edges 1628. The sleeves 1648 and 1650 are formed by overlapping portions of side edges 1626 and 1628 of the front panel 1620 and the back panel 1624 respectively and securing the overlap portions by means gluing, heat bonding, or stitching along sleeve stitch lines 1659 (FIG. 17). As best seen in FIG. 18, the back panel sleeves 1650 may be slightly shorter than front panel, sleeves 1648 so that a portion 1655 of the back panel 1624 extends beyond the back panel sleeve 1650 at the opening end 1661 of the spray bag 1600. The portion 1655 assures that a gap 1653 exists between the back panel sleeves 1650 and the front panel sleeves 1648 sleeves when spray bags 1600 are laid end to end (FIG. 19).

With reference to FIG. 16, the spray bag 1600 is enclosed by stitching the front panel 1620 and the back panel 1624 together along side stitch lines 1664, along fold end stitch line 1662, and along opening end stitch line 1660. Prior to closing the spray bag 1600 by means of opening end stitch line 1660, the spray bag 1600 is filled with ground cover 1614, such as rock material or synthetic particles. In alternative embodiments, the spray bag 1600 may have sleeves 1648 and 1650 only on one side of the spray bag 1600. In addition, the sleeves 1648 and 1650 and the front and back panels 1620 and 1624 may be joined by means other than stitching, including for example gluing.

In order to use the spray bag 1600, the spray bag 1600 is first placed flat on the ground adjacent the foundation 1668 (FIG. 19) of a building and is opened by removing the stitching along side stitch lines 1664, along fold end stitch line 1662, and along opening end stitch line 1660. Once the stitching has been removed, the spray bag 1600 is opened. In FIG. 17, the spray bag 1600 is shown in a partially opened configuration, and the spray bag 1600 is shown in its fully open configuration in FIGS. 18 and 19. Because the front panel 1620 and the back panel 1624 are joined by the fold 1658 that extends beyond the ends of the front panel sleeves 1648 and the back panel sleeves 1650, gaps 1652 R created between adjacent the front panel sleeves 1648 and the back panel sleeves 1650. Once the spray bag 1600 has been laid flat as shown in FIGS. 18 and 19, tubing 1654 is inserted into the sleeves 1648 and 1650. Emitters or spray heads 1656 are then attached to the tubing 1654 where the tubing 1654 is exposed at the gaps 1652 and 1653. With reference to FIG. 19, a liquid pesticide is delivered under pressure through the tubing 1654 to emitters 1656 to thereby create spray patterns 1666 above the ground cover 1614. By periodically treating the ground cover 1614 with the liquid pesticide, insects and other pests may be controlled around the foundation 1668.

The construction of bags 10, 100, 200, and 300 are suitable for use with a method for controlling erosion at the point where a downspout or other conduit discharges water onto the surrounding landscape or where other water runoff channels on a landscape occur. The bags 10, 100, 200, and 300 are constructed of a water permeable, non-degradable material, and the bags 10, 100, 200, and 300 are filled with ground cover, such as rock material or synthetic particles. The water permeable, non-degradable bags 10, 100, 200, and 300 are laid out so that the downspout or other conduit or runoff channel discharges water directly onto the front panels 20 and 22 of the bag 10, the front panels 120 and 122 of the bag 100, the front panel 220 of the bag 200, and the front panel 320 of the bag 300. Because the material of the bags 10, 100, 200, and 300 is water permeable, the water passes into the bags and is dispersed into the surrounding soil through the back panel 24 of the bag 10, the back panel 124 of the bag 100, the back panel 224 of the bag 200, and the back panel 324 of the bag 300. The back panels may be less water permeable than the front panels. The ground cover provides structure for the bag and keeps the back panel of the bag frictionally engaged with the soil below. Alternatively, the water permeable, non-degradable bags 10, 100, 200, and 300 may be open along indicia 34, 36, and 38 of the bag 10, indicia 134, 136, and 138 of the bag 100, indicia 234, 236, and 238 of the bag 200, and indicia 334, 336, and 338 of the bag 300 and unfolded to a flat configuration under the downspout. The ground cover is then spread over the flat bag so that the water discharged from the downspout impinges directly on the ground cover. The ground cover holds the water permeable, non-degradable material of the bag securely against the underlying soil to frictionally engage and hold the soil in place. The bag material can be colored to blend with the landscape when the bag is used unopened, and the ground cover can be sized, shaped, and colored for aesthetic purposes when the bag is used in the opened and flat configuration.

With reference to FIGS. 13-15, and alternative downspout bag 1400 is useful for controlling erosion at the point where a downspout 1300 or other conduit discharges water onto the surrounding landscape or where other water runoff channels on a landscape occur. The downspout bag 1400 is constructed of a water permeable, non-degradable material, and the downspout bag 1400 is filled with ground cover 1414, such as rock material or synthetic particles. The water permeable, non-degradable downspout bag 1400 is positioned under the downspout 1300 or other conduit or runoff channel as shown in FIGS. 13 and 14.

The downspout bag 1400 has a front panel 1420, a back panel (not shown), and an overlying flap 1446. The downspout bag 1400 is enclosed by joining the front panel 1420 to the back panel by means of stitch lines 1464 along sides 1428, by means of an upstream end stitch line 1462 along upstream end 1457, and by means of a downstream end stitch line 1460 along downstream end 1461. The overlying flap 1446 is an extension of either the front panel 1420 or the back panel of the downspout bag 1400. The back panel and the overlying flap 1446 may be less water permeable than the front panel 1420 in order to direct the water flow away from the downspout 1300. Before use, the downspout flap 1446 is folded over onto the front panel 1420 and is temporarily attached to the front panel 1420. In use, the flap 1446 is detached from the front panel 1420 and unfolded into the position shown in FIGS. 14 and 15. The downspout 1300 discharges water directly onto the front panel 1420 of the downspout bag 1400. Because the material of the downspout bag 1400 is permeable, the water passes into the downspout bag 1400 and is dispersed into the surrounding soil through the back panel (not shown) of the downspout bag 1400. The ground cover 1414 provides structure for the downspout bag 1400 and keeps the back panel of the downspout bag 1400 frictionally engaged with the soil below. In addition, the downspout flap 1446 provides a spillway for water that has not soaked through the back panel of the downspout bag 1400 and into the soil below. Consequently, the downspout flap 1446 alleviates soil erosion that might occur at the downstream end 1461 of the downspout bag 1400.

While this invention has been described with reference to preferred embodiments thereof, it is to be understood that variations and modifications can be affected within the spirit and scope of the invention as described herein and as described in the appended claims.

We claim:

1. A method for planting an individual plant in a planting bed of soil:
   a. providing a bag that has a front panel and a back panel having edges and joined along the edges, that is constructed of water permeable, biodegradable bag material, that is filled with a ground cover, and that has indicia for opening the bag;
   b. placing the bag on the planting bed;
   c. opening the bag along the indicia;
   d. unfolding the bag to a flat configuration;
   e. spreading the ground cover over the bag in the flat configuration;
   f. creating an opening through the ground cover on top of the bag and through the bag material into the underlying soil of the planting bed; and
   g. inserting the individual plant into the opening.

2. The method of claim 1, wherein ground cover is selected from the group comprising enriched soil, mulches (organic and inorganic), soil amendment products, and mixtures thereof.

3. The method of claim 1, wherein the indicia for opening the bag is selected from the group comprising bonded seams, sewn seams, tear strips, perforations, and printed cut lines.

4. The method of claim 1, wherein the front panel and the back panel include a lip resulting from folding and securing the material of the front panel and the back panel to itself along the edges of the front panel and the back panel and spreading the ground cover against the lip.

5. The method of claim 1, wherein the front panel and the back panel are rectangular and the indicia is located along three edges of the bag.

6. The method of claim 1, wherein the front panel and the back panel are rectangular and the indicia is located in the front panel and along two end edges of the bag.

7. The method of claim 1, wherein the bag material is selected from the group comprising a sheet of compostable plastic film, paper, cardboard, and cloth fabric.

8. The method of claim 1, wherein the bag material includes an additive selected from the group comprising a fertilizer, a pesticide, an insecticide, an herbicide, and beneficial microbes for release into the underlying soil of the planting bed.

9. A method for establishing a buffer zone along a foundation of a building:
   a. providing a rectangular bag that has a front panel and a back panel joined along four edges, that is constructed of water impermeable, non-degradable bag material, that is filled with a ground cover, and that has indicia for opening the bag;
   b. placing the bag along the foundation;
   c. opening the bag along the indicia;
   d. unfolding the bag to a flat configuration along the foundation; and
   e. spreading the ground cover over the bag in the flat configuration.

10. The method of claim 9, wherein ground cover is selected from the group comprising rock material and synthetic particles.

11. The method of claim 9, wherein in the flat configuration each bag has a bag area and a plurality of bags are placed end-to-end along the foundation and are overlapped before the ground cover is spread over the entire area of each of the bags.

12. The method of claim 9, wherein the indicia for opening the bag is selected from the group comprising bonded seams, sewn seams, tear strips, perforations, and printed cut lines.

13. The method of claim 9, wherein the back panel and the front panel include a lip resulting from folding and securing the material of the back panel and the front panel to itself along the edges of the front panel and the back panel and spreading the enriched soil against the lip.

14. The method of claim 9, wherein the indicia is located along three edges of the bag.

15. The method of claim 9, wherein the indicia is located in the front panel and along two edges of the bag.

16. The method of claim 9, wherein the bag material is selected from the group comprising a water impermeable plastic film, a water impermeable paper material, and a water impermeable cloth fabric.

17. The method of claim 9, wherein the bag material includes an additive selected from the group comprising a pesticide, an insecticide, and an herbicide.

18. A method for preventing erosion of soil adjacent a water discharge opening:
   a. providing a bag that has a front panel and a back panel having edges and joined along the edges, that is constructed of water permeable, non-degradable bag material, that is filled with ground cover, and that has indicia for opening the bag;
   b. placing the bag under the water discharge opening;
   c. opening the bag along the indicia;
   d. unfolding the bag to a flat configuration under the water discharge opening;
   e. spreading the ground cover over the bag in the flat configuration so that the water discharged from the water discharge opening impinges on the ground cover and the back panel of the bag frictionally engages the soil.

19. The method of claim 18, wherein ground cover is selected from the group comprising rock material and synthetic particles.

20. The method of claim 18, wherein the indicia for opening the bag is selected from the group comprising bonded seams, sewn seams, tear strips, perforations, and printed cut lines.

21. The method of claim 18, wherein the front panel and the back panel include a lip resulting from folding and securing the material to itself along the edges of the front panel and the back panel and spreading the ground cover against the lip.

22. The method of claim 18, wherein the front panel and the back panel are rectangular and the indicia is located along three edges of the bag.

23. The method of claim 18, wherein the front panel and the back panel are rectangular and the indicia is located in the front panel and along two edges of the bag.

24. The method of claim 18, wherein the bag material is selected from the group comprising a sheet of perforated plastic and cloth fabric.

25. A method for establishing a pesticide enhanced buffer zone along a foundation of a building:
   a. providing a rectangular bag that is constructed of water impermeable, non-degradable bag material and includes:
      i. a front panel and a back panel releasably joined along opposite side edges, releasably joined along a fold edge, and releasably joined along and opening end edge to form;
      ii. indicia for opening the bag;
      iii. a sleeve attached to at least one side edge; and
      iv. a ground cover inside the bag;
   b. placing the bag along the foundation;
   c. opening the bag along the indicia;
   d. unfolding the bag to a flat configuration along the foundation;
   e. spreading the ground cover over the bag in the flat configuration;
   f. inserting tubing into the sleeve;
   g. connecting emitters to the tubing; and
   h. dispensing pesticide from the emitters onto the ground cover.

26. The method of claim 25, wherein ground cover is selected from the group comprising rock material and synthetic particles.

27. The method of claim 25, wherein when in the flat configuration each bag has a bag area and a plurality of bags are placed end-to-end along the foundation and are overlapped before the ground cover is spread over the entire area of each of the bags.

28. The method of claim 25, wherein the indicia for opening the bag is selected from the group comprising bonded seams, sewn seams, tear strips, perforations, and printed cut lines.

29. The method of claim 25, wherein the front panel and the back panel include a lip resulting from folding and securing the material to itself along the edges of the front panel and the back panel and spreading the ground cover against the lip.

30. The method of claim 25, wherein the indicia is located along three edges of the bag.

31. The method of claim 25, wherein the indicia is located in the front panel and along two edges of the bag.

32. The method of claim 26, wherein the bag material is selected from the group comprising a water impermeable plastic film, a water impermeable paper material, and a water impermeable cloth fabric.

33. The method of claim 26, wherein the bag material includes an additive selected from the group comprising a pesticide, an insecticide, or an herbicide.

* * * * *